United States Patent
Cassani

(10) Patent No.: US 9,801,707 B2
(45) Date of Patent: Oct. 31, 2017

(54) WHIPSTITCHED GRAFT CONSTRUCT AND METHOD OF MAKING THE SAME

(71) Applicant: Mark A. Cassani, Folsom, CA (US)

(72) Inventor: Mark A. Cassani, Folsom, CA (US)

(73) Assignee: ARTHREX, INC., Naples, FL (US)

( * ) Notice: Subject to any disclaimer, the term of this patent is extended or adjusted under 35 U.S.C. 154(b) by 591 days.

(21) Appl. No.: 13/626,270

(22) Filed: Sep. 25, 2012

(65) Prior Publication Data
US 2013/0023927 A1 Jan. 24, 2013

Related U.S. Application Data

(62) Division of application No. 11/723,512, filed on Mar. 20, 2007, now Pat. No. 8,298,284.

(60) Provisional application No. 60/783,866, filed on Mar. 21, 2006.

(51) Int. Cl.
*A61B 19/00* (2006.01)
*A61F 2/08* (2006.01)
*A61B 17/04* (2006.01)

(52) U.S. Cl.
CPC .............. *A61F 2/08* (2013.01); *A61F 2/0811* (2013.01); *A61B 17/0401* (2013.01); *A61F 2002/087* (2013.01)

(58) Field of Classification Search
CPC .......... A61B 17/0401; A61F 2002/087; A61F 2/0811; A61F 2/08
USPC ............... 600/36; 606/22, 79, 228, 232; 623/13.12, 23.72
See application file for complete search history.

(56) References Cited

U.S. PATENT DOCUMENTS

| 5,298,012 | A  | * | 3/1994 | Handlos | 600/36 |
|---|---|---|---|---|---|
| 5,891,168 | A  | * | 4/1999 | Thal | A61B 17/0401 606/139 |
| 6,716,234 | B2 | * | 4/2004 | Grafton et al. | 606/228 |
| 6,730,124 | B2 |   | 5/2004 | Steiner | |
| 2001/0018619 | A1 | * | 8/2001 | Enzerink | A61F 2/08 623/23.72 |
| 2004/0199166 | A1 | * | 10/2004 | Schmieding et al. | 606/79 |
| 2004/0199208 | A1 |   | 10/2004 | Foerster | |
| 2004/0230302 | A1 | * | 11/2004 | May | A61B 17/1714 623/13.12 |
| 2005/0209612 | A1 | * | 9/2005 | Nakao | 606/144 |
| 2006/0058890 | A1 |   | 3/2006 | Lesh | |

* cited by examiner

*Primary Examiner* — Christine H Matthews
*Assistant Examiner* — Joshua D Lannu
(74) *Attorney, Agent, or Firm* — Carlson, Gaskey & Olds

(57) ABSTRACT

A whip stitched graft construct and method of formation. The whip stitched graft construct includes a plurality of tendon strand regions or soft tissue grafts placed together so that at least a portion of the plurality of the tendon strand regions are stitched together by employing multiple suture passes placed according to a whip stitching technique. Preferably, the multiple suture passes start at about the mid length of the plurality of tendon strand regions and are advanced toward one of the free ends of the tendon strands. The whip stitched graft construct is provided with at least two regions, one region formed of at least a plurality of tendon strand regions tied and whip stitched together, and the other region formed of untied segments of the plurality of tendon strands.

25 Claims, 5 Drawing Sheets

WHIPSTITCHED GRAFT CONSTRUCT AND METHOD OF MAKING THE SAME

CROSS-REFERENCE TO RELATED APPLICATIONS

This is a divisional of application Ser. No. 11/723,512, filed Mar. 20, 2007, which claims the benefit of U.S. Provisional Application No. 60/783,866, filed Mar. 21, 2006, the entire disclosures of which are hereby incorporated by reference in their entireties.

FIELD OF THE INVENTION

The present invention relates to methods of surgery and, more specifically, to a method of ligament reconstruction using a whip stitched soft tissue graft construct for attachment to bone.

BACKGROUND OF THE INVENTION

When a ligament or tendon becomes detached from the bone, surgery is usually required to re-secure the ligament or tendon. Often, a substitute ligament or graft is attached to the bone to facilitate regrowth and permanent attachment. The reattachment procedure involves drilling of a graft tunnel between two bones (for example, the tibia and the femur) and securing the substitute ligament or graft in the tunnel.

To achieve optimal results, it is important that the substitute ligament or graft be properly tensioned in the graft tunnel. The tension of the graft prior to fixation must be sufficient in order to achieve stability, but not so excessive that it captures the joint. Tensioning of the graft after the graft is partially in place in the tibial tunnel is also cumbersome.

Accordingly, a need exists for a method for attaching soft tissue to bone which allows the tendon to be securely placed in a bone tunnel and to remain properly tensioned until the ligaments naturally attach to bone. A method of threading suture through a tendon with maximum suture fixation strength, as well as a method of securing the tendon to bone that allows for accelerated tendon healing to bone are also needed.

SUMMARY OF THE INVENTION

The present invention provides a system and method for tendon to bone repair employing a whip stitched graft construct. The whip stitched graft construct of the present invention preferably includes a stitched region formed by employing a suture loop construct with a free floating needle that is attached to the suture loop.

The present invention also provides a whip stitched graft construct that includes a plurality of tendon strand regions (or soft tissue grafts) placed together so that at least a portion of the plurality of the tendon strand regions are stitched together by employing multiple suture passes placed according to a whip stitching technique. Preferably, the multiple suture passes start at about the mid length of the plurality of tendon strand regions and are advanced toward the free ends of the tendon strands. In this manner, the whip stitched graft construct of the present invention is provided with at least two regions, one region formed of at least a plurality of tendon strand regions tied and whip stitched together, and the other region formed of untied or un-stitched segments of the plurality of tendon strands.

The present invention also provides a method of forming a whip stitched graft construct having increased pull-out strength with interference device fixation. The method of the present invention comprises the steps of: (i) providing a plurality of tendon strand regions; and (ii) whip stitching at least a portion of the tendon strand regions by employing a suture strand (preferably a suture loop/needle construct) for stitching the tendon strand regions from about the center of the tendon regions and advancing toward one of the free ends of the tendon strand regions, while leaving untied segments of the tendon strand regions, to form a whip stitched graft construct.

The present invention further provides a method of ligament reconstruction. The method comprises the steps of: (i) providing a target tunnel for ligament reconstruction; (ii) providing a whip stitched graft construct comprising a first region formed of at least a plurality of tendon strands sutured and whip stitched together, and a second region formed of unsutured segments of the plurality of tendon strands; (iii) inserting the whip stitched graft construct into the target tunnel; and (iv) securing the whip stitched graft construct in the tunnel.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

The present invention provides a whip stitched graft construct with increased pull-out strength with interference device fixation and a method of forming such whip stitched graft construct. Graft fixation with the SpeedWhip technique of the present invention reduced the time spent preparing the graft, uniformly compresses the graft, improves the strength of the graft, and allows for last minute adjustments in the length of the graft.

In one embodiment, the whip stitched graft construct of the present invention comprises a stitched region formed by employing a suture loop construct with a free floating needle attached to the suture loop.

In another embodiment, the graft construct of the present invention comprises a plurality of tendon strand regions or soft tissue grafts placed together so that at least a portion of the plurality of the tendon strand regions are stitched together by employing multiple suture passes placed according to a whip stitching technique. The multiple suture passes may be formed by employing, for example, a suture loop construct with a free floating needle attached to the suture loop. Preferably, the multiple suture passes start at about the mid length of the plurality of tendon strand regions and are advanced towards one of the free ends of the tendon strand regions. In this manner, the whip stitched graft construct of the present invention is provided with at least two regions, one region formed of at least a plurality of tendon strand regions tied and whip stitched together, and the other region formed of untied segments of the plurality of tendon strand regions.

Figure 7:
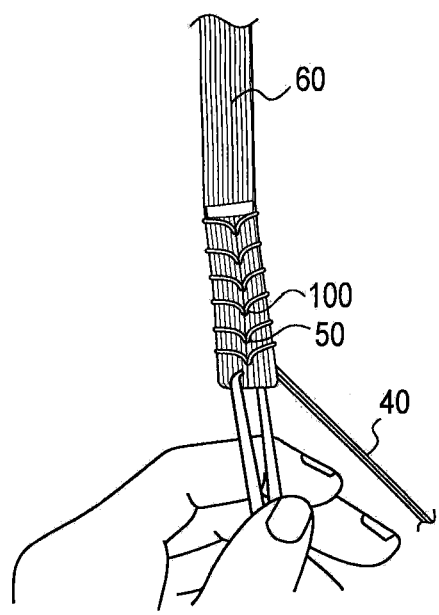
FIG. 7 illustrates a processing step for preparing the whip stitched graft construct of the present invention, and at subsequent step to that shown in FIG. 6.
Figure 8:
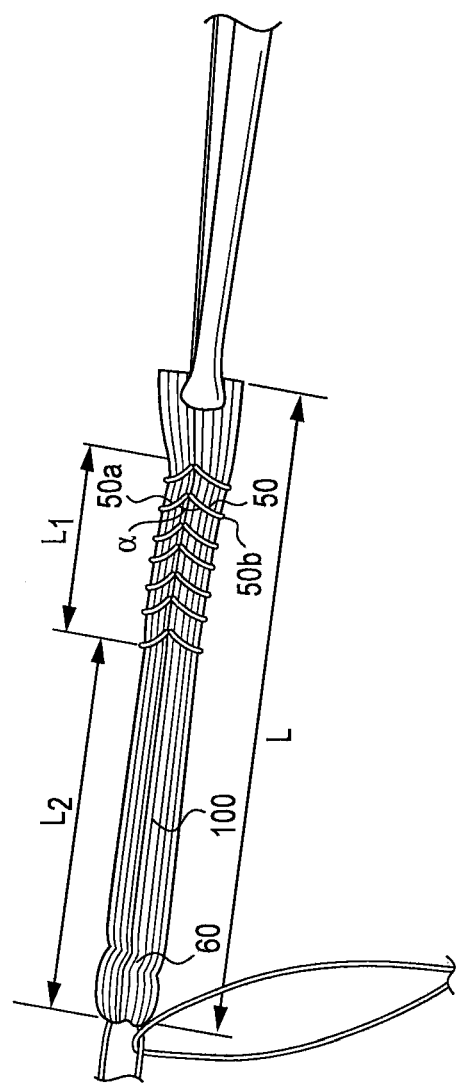
FIG. 8 illustrates another view of the whip stitched graft construct of FIG. 7.
Figure 9:
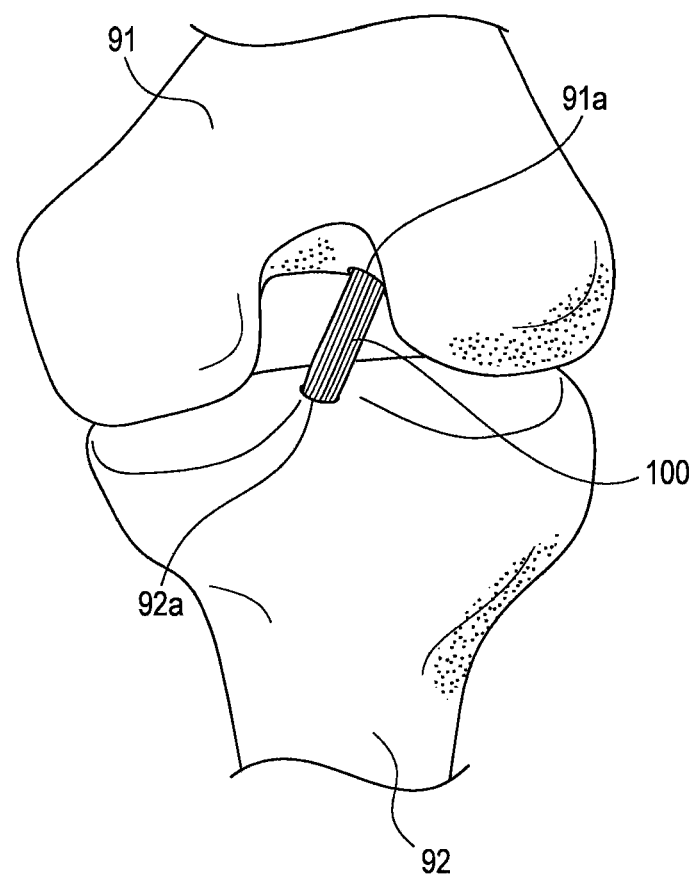
FIG. 9 illustrates the whip stitched graft construct of FIGS. 7 and 8 employed in ACL reconstruction according to a method of the present invention.

Referring now to the drawings, where like elements are designated by like reference numerals, FIGS. 1-8 illustrate a whip stitched graft construct 100 formed according to a method of the present invention. FIG. 9 illustrates the whip stitched graft construct 100 of FIGS. 7 and 8 employed in ACL reconstruction. The technique may be performed with single or multiple bundle grafts.

In an exemplary embodiment, whip stitched graft construct 100 comprises a single tendon strand 30 disposed so that at least a portion 10 of tendon strand 30 is whip stitched around at least another portion 20 of tendon strand 30 according to a technique of the present invention, described below. The single tendon strand 30 may be a tibialis or a semitendonosus strand, among others.

Although the invention will be described with reference to a single tendon strand having two tendon strand regions that are whip stitched according to an embodiment of the present invention, the invention is not limited to this embodiment and encompasses embodiments where a plurality of single tendon strands are whip stitched according to a method of the present invention.

Figure 1:
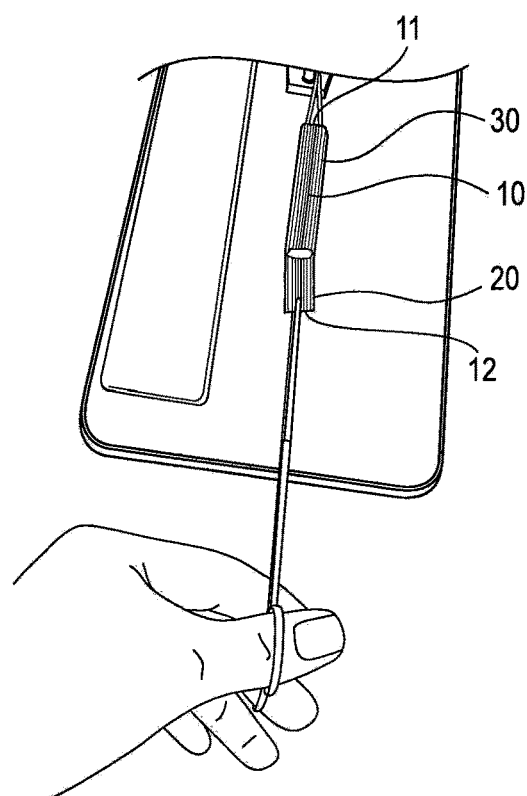
FIG. 1 illustrates a processing step for preparing a whip stitched graft construct in accordance with an embodiment of the present invention.

FIG. 1 illustrates a working station with a preparation area having a soft tissue graft comprising single tendon strand 30 folded in half at end 11 of the preparation area, so that regions 10, 20 of the tendon strand are securely affixed to the end 11. As shown in FIG. 1, opposite ends 12 of the graft tendon regions are held by hand and/or by employing a clamp, for example. Alternatively, the opposite ends 12 of the graft can be also affixed to the preparation area but in a way that allows the graft to be easily released to pass a suture loop over the graft.

Subsequent to the graft fixation at the work station, a flexible strand is provided in the vicinity of the preparation area and of the graft. According to an exemplary embodiment of the invention, the flexible strand may be a suture loop/needle construct 55 (FIG. 3a) that includes a continuous loop 40 of suture (preferably a continuous loop of #2 FiberWire suture, sold by Arthrex, Inc. of Naples, Fla.) attached to a free floating thin needle 41. In an exemplary embodiment, the needle 41 is a thin nitinol needle that allows an increased number of suture loop passes through, or around, the tissue to be attached or sutured with decreased trauma.

Figure 3:
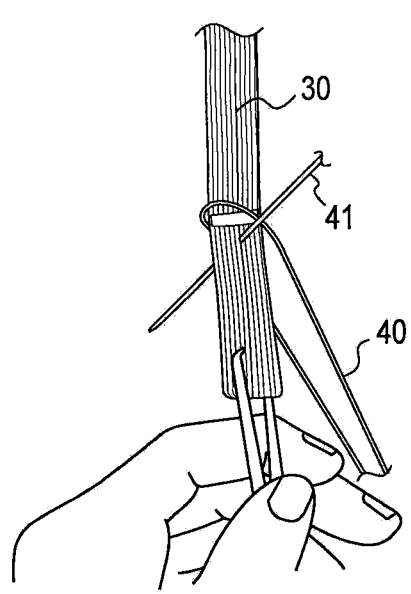
FIG. 3 illustrates a processing step for preparing the whip stitched graft construct of the present invention, and at subsequent step to that shown in FIG. 2.
Figure 3A:
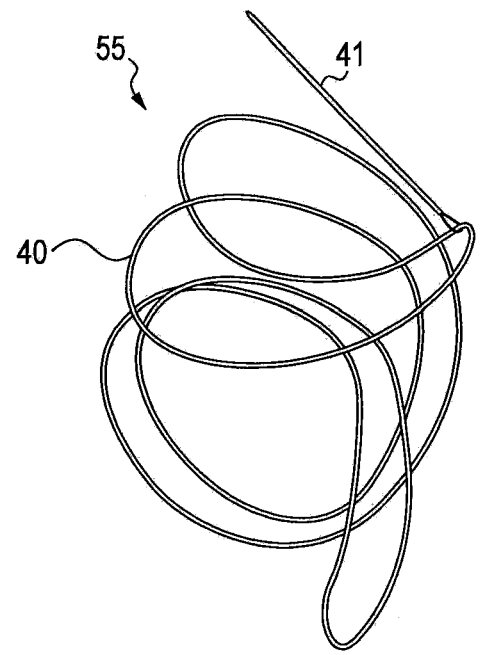
FIG. 3a illustrates an exemplary suture loop/needle construct employed for the formation of the whip stitched graft construct of the present invention.

The thin needle is preferably straight and easy to handle, without instruments. The needle moves freely on the suture 40 to recenter itself after passing through tissue and to facilitate even tensioning. As shown in FIG. 3a, the free floating needle 41 is not swaged on the suture 40 so, after passing the suture loop construct 55 through the tissue to be treated, the needle 41 may be recentered if the suture strands are uneven. Details of the suture loop/needle construct 55 employed in the present invention are described in U.S. Provisional Appl. Ser. No. 60/834,191 filed on Jul. 31, 2006 and entitled "Suture Loop Construct with Free Floating Needle and Method of Surgery."

Figure 2:
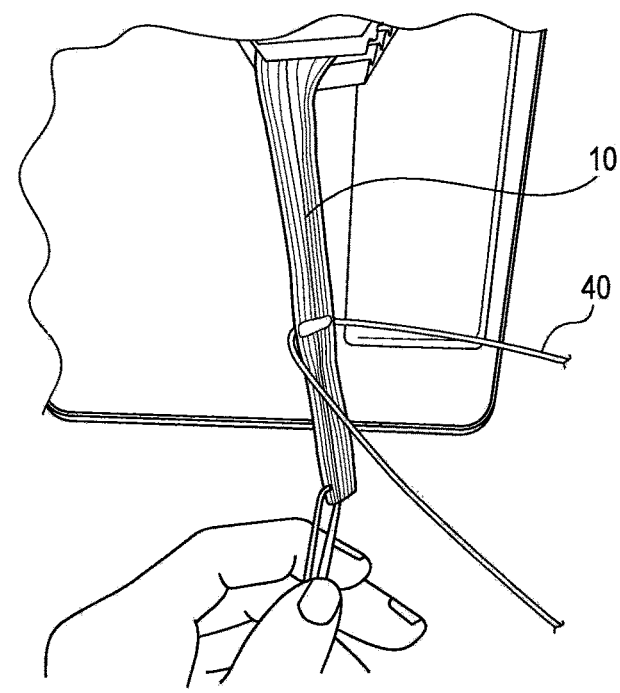
FIG. 2 illustrates a processing step for preparing the whip stitched graft construct of the present invention, and at subsequent step to that shown in FIG. 1.

Flexible suture loop (FiberLoop) 40 attached to free needle 41 is passed over the free ends 12 of the graft tendon, as shown in FIG. 2. The needle 41 is then passed through the graft tendon regions 10, 20 at a proximal starting point which, in an exemplary embodiment only, is located at about the center of the graft tendon regions (FIG. 3). As described below, the graft tendon regions will be stitched together starting from the center and moving toward the ends 12 of the graft.

The suture forming the continuous loop 40 employed in the method of the present invention may be formed of any flexible material. In the preferred embodiment, the sutures are formed of a high strength suture material such as FiberWire suture, sold by Arthrex, Inc. of Naples, Fla., and described in U.S. Pat. No. 6,716,234, the disclosure of which is incorporated by reference herein. The high strength suture may be available in various lengths and, preferably, is a #2 FiberWire suture strand. FiberWire suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire suture includes a core within a hollow braided construct, the core being a twisted yarn of UHMWPE. The suture may optionally include filaments of various colors.

Figure 4:
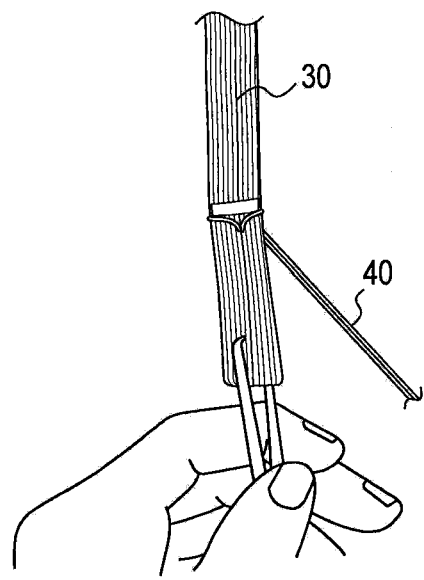
FIG. 4 illustrates a processing step for preparing the whip stitched graft construct of the present invention, and at subsequent step to that shown in FIG. 3.
Figure 5:
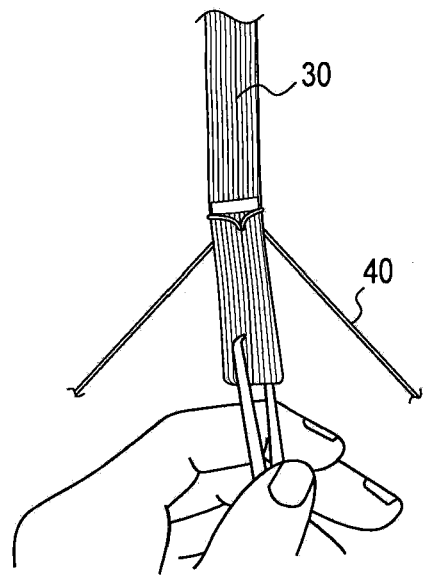
FIG. 5 illustrates a processing step for preparing the whip stitched graft construct of the present invention, and at subsequent step to that shown in FIG. 4.
Figure 6:
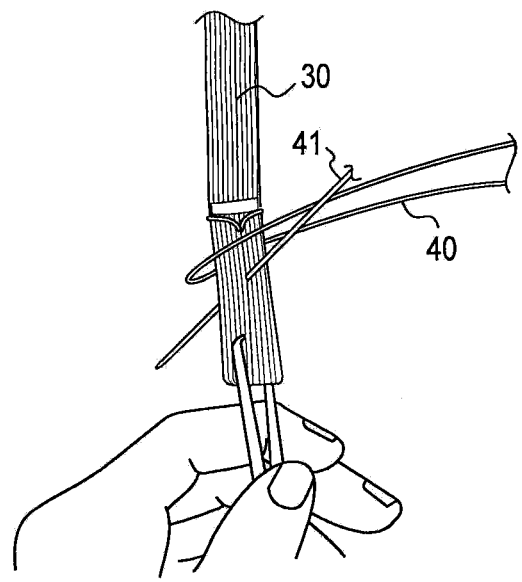
FIG. 6 illustrates a processing step for preparing the whip stitched graft construct of the present invention, and at subsequent step to that shown in FIG. 5.

Referring now to FIGS. 4 and 5, after passing and tensioning the first stitch, the suture strands are spread on either side of the graft, dropping the graft between the strands. The needle 41 is then passed through the graft tendon regions, distal to the first pass (i.e., towards the ends 12 of the graft tendon regions), as shown in FIG. 6. Preferably, the needle 41 is inserted on the same side of the graft with each pass.

This process is repeated until a desired stitching length is obtained. For example, FIGS. 7 and 8 illustrates a first stitched region 50 of the graft construct 100 comprising single tendon strand regions 10, 20 sutured together by the method described above and having a first stitching length $L_1$. A second region 60 of the graft construct 100 comprises segments of the single tendon strand regions 10, 20 that are not stitched. As shown in FIG. 8, the stitching length $L_1$ of the first stitched region 50 is about half the length L of the graft tendon regions 10, 20. However, the invention contemplates any desired stitching length of the stitched region 50, depending upon the graft tendon characteristics and the specifics of each surgical intervention. For example, and according to an exemplary embodiment, the stitching length $L_1$ may be about equal to, or less than, the length L of the graft tendon regions 10, 20.

As shown in FIG. 8, the stitched region 50 of the graft construct 100 has a particular stitching configuration, with suture rows 50*a* forming an angle α with suture rows 50*b*. Preferably, angle α is about 150 to about 45 degrees, more preferably of about 120 to about 90 degrees. As also shown in FIG. 8, each suture row (thread) 50*a* intersects a corresponding suture row (thread) 50*b* at about the mid width of the graft construct 100, to form a symmetrical stitching. Although the invention has been described above with reference to the formation of stitched region 50 having the stitched configuration shown in FIG. 8, the invention is not limited to this exemplary embodiment, and contemplates embodiments wherein the stitched region 50 is formed by any stitching technique and with any angle α, or a combination of different stitching techniques, as long as the graft construct comprises single tendon strands tied or bound together for at least a part of the length of the final graft construct. Angle α may also vary relative to different rows (threads) of the stitching. The invention also contemplates embodiments wherein the stitching is asymmetrical relative to the longitudinal axis of the graft construct. In these various exemplary embodiments, the flexible strand forming the stitched region may be FiberWire, for example.

In addition, the invention also contemplates a graft construct comprising alternating regions of stitched regions (such as stitched region 50) and non-stitched regions (such as region 60). For example, the graft construct may comprise a plurality of stitched regions disposed adjacent a plurality of non-stitched regions. The stitched regions may be formed by employing a flexible strand (for example, a suture strand), or by employing a suture loop/needle construct (such as the suture loop/needle construct 55 of FIG. 3*a*), or a combination of techniques employing a flexible strand and a suture loop/needle construct.

A graft construct having a non-stitched region with each end bound by a stitched region may be formed by the stitching technique described above, but with a starting point not at about the center of the graft, but at about one third the length of the graft. In this embodiment, once the graft (or plurality of single graft tendons) is fixated at the work station, a suture loop/needle construct (comprising a suture loop on a free floating needle, for example) is passed over the free end of the graft tendons (the first end) at a starting point which, in an exemplary embodiment, is located at about one third of the length of the graft tendons. The graft tendons are stitched together starting from about the third of their length and moving toward the end of the graft. After passing and tensioning the first stitch, the suture loop is again passed over the free end of the graft and the needle is passed through the graft tendons, distal to the first pass (i.e., towards the first end of the graft tendons). This process is repeated until a first stitched region is obtained. The graft is then released from the work station, and the other end of the graft (the second end) is subsequently fixated at the work station. Stitching of the other end of the graft is conducted in a manner similar to that for the formation of the first stitched region, also starting from about the third of the length of the tendons and moving toward the second end of the graft. The suture loop may be formed of a continuous #2 FiberWire, for example, and may be attached to a thin straight Nitinol needle. The resulting graft construct comprises a non-stitched region located between two stitched regions.

Although FIGS. 1-8 illustrate graft construct 100 comprising a single tendon strand 30 (with regions 10, 20 of about equal length), the invention is not limited to this exemplary embodiment and encompasses embodiments wherein the graft construct is formed of any number of such single tendon strands.

Subsequent to the stitching operation, the needle may be cut off and the suture loop maintained or, alternatively, cut more proximal to give two free ends of suture. If a last minute length change to the stitched area of the graft is needed, then the distal passes of suture may be unthreaded and the graft cut to size.

Stay sutures may be optionally placed at the end of the graft segments for tensioning the graft pre-operatively, for pulling the graft into bone tunnels at surgery, or for general ease of handling throughout the graft preparation process. The stay sutures, for example #2 FiberWire suture, firmly apply balanced tension to the tendon upon tightening.

A method of ligament reconstruction employing the whip stitched graft construct 100 of the present invention comprises the steps of: (i) providing a target tunnel for ligament reconstruction; (ii) providing a whip stitched graft construct 100 comprising a first stitched region 50 formed of at least a plurality of tendon strand regions 10, 20 sutured and whip stitched together, and a second region 60 formed of unsutured segments of the plurality of tendon strands; (iii) inserting the whip stitched graft construct 100 into the target tunnel; and (iv) securing the whip stitched graft construct 100 in the tunnel.

FIG. 9 illustrates a schematic view of a knee undergoing ACL reconstruction employing the whip stitched graft construct 100 formed according to an embodiment of the present invention. As illustrated in FIG. 9, whip stitched graft construct 100 is secured within femoral and tibial tunnels (sockets) 91*a*, 92*a*, each formed in femur 91 and tibia 92, respectively.

The femoral and tibial tunnels (sockets) 91*a*, 92*a* may be formed by a known technique, or alternatively, by using a retrodrill technique. According to the retrodrill technique, the tibial or femoral sockets are prepared by employing a retrodrill device provided with a retrodrill cutter detachable from a retrodrill guide pin, in the manner described in U.S. Patent Application Publication No. 2004/0199166, entitled "ACL Reconstruction Technique Using Retrodrill." As described in U.S. Patent Application Publication No. 2004/0199166, a retrodrill device for ACL reconstruction is provided with a retrodrill cutter detachable from a retrodrill guide pin. The retrodrill cutter is inserted in a retrograde manner through the tibia or femur by employing a retrodrill guide pin provided with depth markings.

Preferably, the step of securing the whip stitched graft construct 100 in at least the tibial and femoral sockets or tunnels may be accomplished by plugging the target tunnel with a synthetic plug, bone plug or screw to contain and secure the whip stitched graft construct 100 in the tunnel or, alternatively, by employing knotless lateral fixation using, for example, two knotless fixation devices (such as two Arthrex PushLock anchors). The fixation devices may be preferably formed of a translucent or transparent polymer material, preferably bioabsorbable materials such as polyglycolic or polylactic acid polymers.

According to yet another embodiment, graft insertion and fixation may be conducted by employing a continuous loop/button construct provided with a button, preferably of titanium alloy, and a continuous loop attached to the button. The button has an oblong configuration and a width that is preferably less than about 1 mm narrower than the width of the drill hole through which the button is inserted and subsequently passed through. The button is provided with an inside eyelet that allows the passage of the continuous loop. In an exemplary embodiment, the suture loop may be a single high strength suture such as FiberWire® suture. In another exemplary embodiment, the continuous loop may be formed of a plurality of suture strands configured to separate from a single strand to a plurality of strands in a continuous loop.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed as new and desired to be protected by Letters Patent of the United States is:

1. A method of threading suture through a tendon strand, the method comprising the steps of:
    positioning a tendon strand in a vicinity of a work station;
    folding over the tendon strand to form a folded tendon;
    beginning a stitched region of the folded tendon at a location of the folded tendon that is between one-third and one-half of a total length of the folded tendon by threading a flexible strand through the folded tendon; and
    forming a plurality of threads by advancing the flexible strand toward an end of the folded tendon and in a direction away from the work station, wherein the flexible strand includes a continuous loop of suture attached to a needle.

2. The method of claim 1, wherein the needle is a free floating needle.

3. The method of claim 1, wherein the flexible strand is formed of ultrahigh molecular weight polyethylene.

4. The method of claim 1, wherein the threads are provided in a plurality of rows, at least two of the rows being about parallel to each other.

5. The method of claim 1, wherein the continuous loop of suture excludes free ends.

6. A method of forming a graft, comprising:
    positioning a graft through an opening of a suture loop of a suture loop/needle construct, the graft including a tendon strand with a first side and a second side;
    inserting a needle of the suture loop/needle construct through the tendon strand from the first side to the second side to create a first stitched region of the graft;
    positioning the graft through the opening of the suture loop again; and
    inserting the needle through the tendon strand at the first side to create a second stitched region of the graft that is distal to the first stitched region.

7. The method of claim 6, comprising repeating the steps of positioning the graft and inserting the needle through the tendon strand until a desired stitching length is obtained.

8. The method of claim 6, comprising fixating the graft to a work station.

9. The method of claim 6, comprising repeating the steps of positioning the graft and inserting the needle through the tendon strand on a different section of the graft to create additional stitched regions.

10. The method of claim 6, wherein at least one of the first stitched region and the second stitched region includes a first suture row that forms an angle relative to a second suture row.

11. The method of claim 6, comprising leaving portions of the graft unstitched.

12. The method of claim 6, wherein the suture loop is a continuous loop of suture attached to the needle.

13. The method of claim 6, comprising employing the graft in a ligament reconstruction after creating the first stitched region and the second stitched region.

14. The method of claim 6, wherein the suture loop is a continuous loop of suture that excludes free ends.

15. A method of forming a graft, comprising:
    passing a suture loop of a suture loop/needle construct at least partially over a graft, the graft including a tendon strand, wherein passing the suture loop includes spreading suture strands of the suture loop apart and then positioning the suture strands around the graft such that the graft extends between the suture strands;
    inserting a needle of the suture loop/needle construct through the tendon strand to create a first stitched region of the graft;
    passing the suture loop at least partially over the graft again; and
    inserting the needle through the tendon strand to create a second stitched region of the graft that is distal to the first stitched region.

16. The method of claim 15, comprising holding the graft with a clamp.

17. The method of claim 15, comprising repeating the steps of passing the suture loop at least partially over the graft and inserting the needle through the tendon strand until a desired stitching length is obtained.

18. The method of claim 17, comprising cutting off the needle of the suture loop/needle construct after obtaining the desired stitching length.

19. The method of claim 15, comprising folding the graft in half such that graft end regions of the graft are overlapping.

20. The method of claim 19, wherein the first stitched region and the second stitched region attach the graft end regions together.

21. The method of claim 19, wherein passing the suture loop includes positioning the suture strands around the graft end regions.

22. The method of claim 19, wherein inserting the needle through the tendon strand includes passing the needle through each of the graft end regions.

23. The method of claim 15, wherein the needle is inserted on a same side of the tendon strand each time the suture loop/needle construct is threaded through the tendon strand when forming the first stitched region and the second stitched region.

24. The method of claim 15, wherein the needle is a free floating needle.

25. The method of claim 15, wherein at least a portion of the graft is unstitched.

* * * * *